United States Patent [19]

Markstein

[11] Patent Number: 5,955,468

[45] Date of Patent: Sep. 21, 1999

[54] BENZO[G]QUINOLINES FOR USE IN PREVENTION OR DELAY OF PROGRESSIVE ATROPHY OF THE OPTIC NERVE

[75] Inventor: Rudolf Markstein, Rheinfelden, Germany

[73] Assignee: Sandoz Ltd., Basel, Switzerland

[21] Appl. No.: 08/466,505

[22] Filed: Jun. 6, 1995

Related U.S. Application Data

[63] Continuation of application No. 08/360,159, Dec. 20, 1994, abandoned.

[30] Foreign Application Priority Data

Dec. 21, 1993 [DE] Germany ............... 93 26 010

[51] Int. Cl.⁶ ............... C07D 401/12; A61K 31/435
[52] U.S. Cl. ............... 514/290; 546/101
[58] Field of Search ............... 546/101; 514/290

[56] References Cited

U.S. PATENT DOCUMENTS 5,262,422 11/1993 Gull et al. ............... 514/290

*Primary Examiner*—Alan L. Rotman
*Attorney, Agent, or Firm*—Robert S. Honor; Melvyn M. Kassenoff; Thomas O. McGovern

[57] ABSTRACT

Compounds of formula I

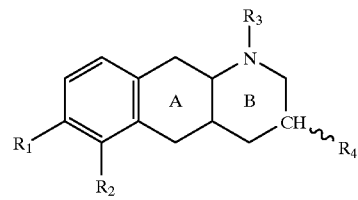

wherein A, B, $R_1$, $R_2$, $R_3$ and $R_4$ are as defined in the description, are useful for the treatment of conditions where prevention or delay of progressive atrophy of the optic nerve is desirable.

9 Claims, No Drawings

BENZO[G]QUINOLINES FOR USE IN PREVENTION OR DELAY OF PROGRESSIVE ATROPHY OF THE OPTIC NERVE

This is a continuation of application Ser. No. 08/360,159, filed on Dec. 20, 1994 now abandoned.

The present invention relates to a new pharmaceutical use of 1, 2, 3, 4, 4a, 5, 10, 10a-octahydro-benzo[g]quinoline derivatives.

More particularly the present invention relates to a new pharmaceutical use for compounds of formula I

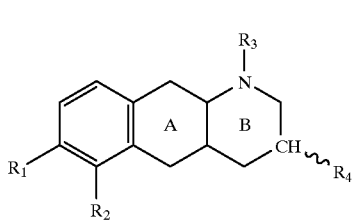

(I)

wherein
the rings A and B are trans-fused and wherein
$R_1$ and $R_2$ are each independently hydrogen, hydroxy or methoxy, with the proviso that $R_1$ and $R_2$ may not both be hydrogen;
$R_3$ is hydrogen or $C_{1-4}$alkyl;
$R_4$ is —COOH, —$CH_2OR_5$, —$CH_2CN$, —$CON(R_6)R_7$, —$CH_2SR_8$, —$NHSO_2N(R_9)R_{10}$ or —NH—$CON(R_9)R_{10}$,
$R_5$ is hydrogen or $C_{1-3}$alkyl,
$R_6$ is hydrogen or $C_{1-3}$alkyl and
$R_7$ is hydrogen, $C_{1-3}$alkyl, phenyl or pyridyl, said phenyl or pyridyl being optionally substituted by halogen, methyl or methoxy or
$R_6$ and $R_7$ together are —$(CH_2)_4$—, —$(CH_2)_5$— or —$(CH_2)_2$—O—$(CH_2)_2$—,
$R_8$ is $C_{1-4}$alkyl or pyridyl, said pyridyl being optionally substituted by halogen, methyl or methoxy, and
$R_9$ and $R_{10}$ are each independently hydrogen or $C_{1-3}$alkyl or together are —$(CH_2)_4$— or —$(CH_2)_5$—, as well as the physiologically-hydrolysable and -acceptable esters thereof.

The compounds of formula I exist in free and in salt form, e.g. as acid addition salts or, when e.g. $R_4$ is carboxy, as internal salts.

The compounds of formula I as well as the physiologically-hydrolysable and -acceptable esters thereof, in free or in pharmaceutically acceptable salt form, are hereinafter referred to as "the compounds".

It will be understood that the compounds include all possible individual isomers as well as racemates and other isomeric mixtures.

The compounds as well as their production process are known e.g. from U.S. Pat. No. 4,565,818. This patent also discloses the use of the compounds as prolactin secretion inhibiting agents e.g. in the treatment of conditions or disorders for which reduction of prolactin secretion levels is indicated, furthermore as dopaminergic agents e.g. in the treatment of Morbus Parkinson and as dopamine receptor stimulating agents e.g. in the treatment or prophylaxis of coronary diseases.

The compounds also include the (–)-(3β, 4aα, 10aβ)-1, 2, 3, 4, 4a, 5,10,10a-octahydro-3-[(2-pyridylthio)methyl]-1-methyl-6-hydroxy-benzo[g]quinoline which is of formula I but is not specifically disclosed in the above mentioned U.S. patent. This compound (hereinafter referred to as compound A) in free form or acid addition salt form as well as its production process are known e.g. from U.S. Pat. No. 5,262,422. This patent discloses the use of compound A in the treatment of glaucoma, Morbus Parkinson, depression and cocaine dependency.

The use of compound A in the treatment of glaucoma is based on its ability to lower intra-ocular blood pressure.

In accordance with the present invention, it has now surprisingly been found that the compounds increase the blood flow in the optic nerve.

The increase of blood flow in the optic nerve is indicated by experiments performed as described by M. Rudin and A. Sauter in Noninvasive determination of regional cerebral blood flow in rats using dynamic imaging with Gd(DTPA), Magnetic Res. in Med. 22, 32–46 (1991). In this test, rats are anesthetized with isoflurane. The femoral vein is cannulated for injection of the paramagnetic contrast agent Gd(diethylentriaminepenta-acetate). Determination of blood flow (ml/100/min.) by NMR imaging is performed immediately before and 30 min. after s.c. drug administration. Experiments are performed double blind in groups of 7–9 animals. In a first series of experiments, the whole optic nerve is measured. In a second series, the effect on subregions of the optic nerve including the proximal part with the head of the optic nerve is determined.

In this test compound A at a dose of 0.1 mg/kg s.c. significantly improves blood flow to the proximal optic nerve by almost 30% (measured 30 min. after drug administration) whereas Timolol, the most widely used drug for the therapy of glaucoma, does not show any improvement in optic nerve perfusion at 0.5 mg/kg s.c. In the second series of experiments, compound A markedly enhances blood perfusion in the proximal part of the optic nerve including the head and in the distal part whereas Timolol had no significant effect in both subregions of the rat optic nerve.

The compounds are therefore useful in conditions where prevention or delay of progressive atrophy of the optic nerve is desirable, for example in conditions where the visual fields are impaired and particularly in glaucoma.

It is to be noted that the compounds are useful in particular in glaucoma forms which are not characterized by an increase of the intra-ocular pressure (low tension glaucoma), in which standard glaucoma therapy including β-blockers, in particular Timolol, is useless.

It is also to be noted that the above described ability to increase the optic nerve perfusion is totally unexpected not only for the compounds which have never been suggested as antiglaucoma agents but also for compounds like compound A which exhibit intra-ocular blood pressure lowering and have therefore been suggested for the treatment of glaucoma.

Drugs which like compound A and unlike Timolol improve both elevated intra-ocular pressure and impaired blood flow in the optic nerve are expected to possess disease-modifying properties, which is of particular interest.

For the above-mentioned indications the appropriate dosage will of course vary depending upon, for example, the compound employed, the host, the mode of administration and the nature and severity of the condition being treated. However, in general, satisfactory results in animals are indicated to be obtained at a daily dosage of from about 0.01 to about 1 mg/kg animal body weight. In larger mammals, for example humans, an indicated daily dosage is in the range from about 0.25 to about 10 mg of a compound according to the invention conveniently administered, for example, in divided doses up to four times a day.

The compounds may be administered in any usual manner, e.g. orally, for example in the form of tablets or capsules, or parenterally, for example in the form of injection solutions or suspensions.

For the treatment of glaucoma, the compounds are preferably applied topically to the eye in ca. 0.002 to ca. 0.02% ophthalmological solutions. The ophthalmic vehicle is such that the compound is maintained in contact with the ocular surface for a sufficient time period to allow the compound to penetrate the corneal and internal regions of the eye. The pharmaceutically acceptable ophthalmic vehicle may be e.g. an ointment, vegetable oil, or an encapsulating material. Compound A is suitably administered in form of its hydrochloride.

The present invention also provides pharmaceutical compositions comprising the compounds in association with at least one pharmaceutical carrier or diluent for use in the treatment of glaucoma. Such compositions may be manufactured in conventional manner. Unit dosage forms may contain for example from about 0.05 mg to about 5 mg of the compound.

The invention further provides the use of a compound according to the invention for the manufacture of a pharmaceutical composition for the treatment of conditions where prevention or delay of progressive atrophy of the optic nerve is desirable, in particular glaucoma.

The invention futhermore provides a method for the treatment of conditions where prevention or delay of progressive atrophy of the optic nerve is desirable, in particular glaucoma, in a subject in need of such treatment, which comprises administering to said subject a therapeutically effective amount of a compound according to the invention.

EXAMPLE

Eye Drops

An injection solution containing the ingredients indicated below is prepared by conventional techniques and is useful in the treatment of glaucoma:

| Composition | | mg/ml |
|---|---|---|
| Compound A in hydrochloride form | | 1.107 |
| Glycerol | | 25.0 |
| Benzalkonium chloride | | 0.105 |
| Hydroxypropylmethylcellulose | | 1.0 |
| Water for injection | to | 1.0 ml |

What we claim is:

1. A method of increasing blood flow in the optic nerve in a subject in need of said treatment, which comprises administering to the subject in an amount effective to increase blood flow in the optic nerve a compound of the formula

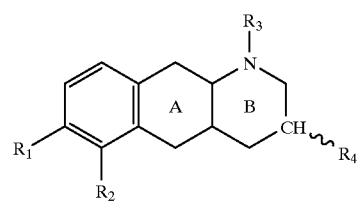

wherein
the rings A and B are trans-fused and wherein $R_1$ and $R_2$ are each independently hydrogen, hydroxy or methoxy, with the proviso that $R_1$ and $R_2$ may not both be hydrogen;
$R_3$ is hydrogen or $C_{1-4}$alkyl;
$R_4$ is —COOH, —CH$_2$OR$_5$, —CH$_2$CN, —CON(R$_6$)R$_7$, —CH$_2$SR$_8$, —NHSO$_2$N(R$_9$)R$_{10}$ or —NH—CON(R$_9$)R$_{10}$,
$R_5$ is hydrogen or $C_{1-3}$alkyl,
$R_6$ is hydrogen or $C_{1-3}$alkyl and
$R_7$ is hydrogen, $C_{1-3}$alkyl, phenyl or pyridyl, said phenyl or pyridyl being optionally substituted by halogen, methyl or methoxy or
$R_6$ and $R_7$ together are —(CH$_2$)$_4$—, —(CH$_2$)$_5$— or —(CH$_2$)$_2$—O—(CH$_2$)$_2$—,
$R_8$ is $C_{1-4}$alkyl or pyridyl, said pyridyl being optionally substituted by halogen, methyl or methoxy, and
$R_9$ and $R_{10}$ are each independently hydrogen or $C_{1-3}$alkyl or together are —(CH$_2$)$_4$— or —(CH$_2$)$_5$—,
or a physiologically-hydrolyzable and -acceptable ester thereof, in free base or in pharmaceutically acceptable salt form.

2. A method according to claim 1 in which the compound is other than in ester form.

3. The method according to claim 1 in which the compound is the (−)-(3β, 4aα, 10aβ)-1,2,3,4,4a,5,10, 10a-octahydro-3-[(2-pyridylthio)methyl]-1-methyl-6-hydroxy-benzo[g]quinoline in free form or pharmaceutically acceptable acid addition salt form.

4. The method according to claim 2 in which the compound is the (−)-(3β, 4aα, 10aβ)-1, 2,3,4,4a,5,10, 10a-octahydro-3-[(2-pyridylthio)methyl]-1-methyl-6-hydroxy-benzo[g]quinoline in hydrochloride salt form.

5. A method according to claim 1 in which 0.01 to 1 mg/kg of animal body weight of the compound is administered daily.

6. A method according to claim 1 in which 0.25 to 10 mg of the compound are administered daily.

7. A method according to claim 1 in which 0.05 to 5 mg of the compound are administered per unit dose.

8. A method according to claim 1 in which the compound is administered in a ophthalmological pharmaceutical composition comprising 0.002% to 0.02% of the compound and a pharmaceutically acceptable ophthalmological carrier therefor.

9. A method according to claim 1, wherein the subject in need of said treatment has low tension glaucoma.

* * * * *